(12) United States Patent
Ciliberto et al.

(10) Patent No.: US 6,521,426 B1
(45) Date of Patent: Feb. 18, 2003

(54) PREPARATION OF RECOMBINANT ADENOVIRUS CARRYING A REP GENE OF ADENO-ASSOCIATED VIRUS

(75) Inventors: Gennaro Ciliberto, Rome (IT); Stefano Colloca, Rome (IT); Nicola La Monica, Rome (IT)

(73) Assignee: Istituto Di Ricerche Di Biologia Molecolare P. Angeletti S.p.A., Pomezia (IT)

( * ) Notice: Subject to any disclaimer, the term of this patent is extended or adjusted under 35 U.S.C. 154(b) by 0 days.

(21) Appl. No.: 09/647,795
(22) PCT Filed: Apr. 8, 1999
(86) PCT No.: PCT/EP99/02384
§ 371 (c)(1), (2), (4) Date: Dec. 8, 2000
(87) PCT Pub. No.: WO99/53084
PCT Pub. Date: Oct. 21, 1999

(30) Foreign Application Priority Data

Apr. 8, 1998 (WO) .............................. PCT/IT98/00082
Jun. 24, 1998 (GB) ............................................. 9813670

(51) Int. Cl.$^7$ .......................... C12P 21/04; C12P 21/06; A61K 39/225
(52) U.S. Cl. .................. 435/70.1; 435/69.1; 424/233.1
(58) Field of Search ............................. 435/69.1, 70.1; 424/233.1

(56) References Cited

FOREIGN PATENT DOCUMENTS

| WO | WO 96/13598 A2 | * | 5/1996 |
| WO | WO 97/45550 A2 | * | 12/1997 |

OTHER PUBLICATIONS

Recchia, A., et al., Site–specific integration mediated by a hybrid adenovirus/adeno–associated virus vector, Proc. Natl. Acad. Sci. USA, 96:2615–2620, Mar. 1999.*

* cited by examiner

Primary Examiner—Hankyel T. Park
Assistant Examiner—Stacy Brown
(74) Attorney, Agent, or Firm—Anna L. Cocuzzo; Jack L. Tribble

(57) ABSTRACT

Adenoviral particles are produced by incubating cells containing a helper adenovirus vector and a helper-dependent adenoviral vector including an Adeno-Associated Virus (AAV) rep gene, such as rep 78. Cells are provided containing a helper adenovirus vector. A helper-dependent adenoviral vector including an AAV rep gene is introduced into the cells, for instance by infection with infective viral particles. The cells are incubated to produce adenoviral particles containing nucleic acid including the AAV rep gene. Advantageously, cells containing helper adenovirus vector are pre-incubated for 0.5–12 hours, preferably about 4 hours, to allow expression of viral proteins required for adenoviral genome replication before introducing the helper-dependent adenovirus vector including an AAV rep gene.

13 Claims, 1 Drawing Sheet

A

B

A

B

PREPARATION OF RECOMBINANT ADENOVIRUS CARRYING A REP GENE OF ADENO-ASSOCIATED VIRUS

BACKGROUND OF THE INVENTION

The present invention relates to viral vectors which may be used in gene delivery, such as in gene therapy, processes for viral replication, and viral vectors, cells and cell lines useful in preparation of viral vectors which may be used in gene delivery. The invention is not concerned with gene therapy itself, rather with the provision and production of vectors which may be used in gene delivery, such as in gene therapy.

The integration of therapeutic genes into specific locations of the DNA of dividing and non-dividing cells, accompanied by prolonged expression, is the optimal strategy for somatic gene therapy.

Adeno-associated virus (AAV) has the unique capacity of preferentially integrating its viral DNA within a defined region of the cellular genome, thus reducing the risks of insertional mutagenesis associated with other viruses such as retroviruses that integrate at random positions.

AAV is a non-pathogenic human parvovirus which usually requires Adenovirus (Ad) or Herpes virus as a helper to replicate efficiently. In the absence of helper virus the AAV genome integrates into host-cell genomic DNA at high frequency. Analysis of flanking sequences from latently infected cells of human origin have revealed integration of the AAV genome into a specific locus in 60–70% of cases. The integration locus (aavs1) has been sequenced and localised to human chromosome 19q13.3-qter (Kotin, R M, et al, 1990; Samulski. R J et al, 1991).

The integrated AAV genome can be rescued and replicated if cells containing an integrated provirus are superinfected with a helper virus such as Ad.

Parks et al., (1996) describe a Ad system in which a helper virus provides in trans all viral proteins required for propagation of the vector, which contains only the cis acting elements relevant for DNA replication and packaging (inverted terminal repeats and packaging signal). These two elements are contained within about 500 bp located at the end of viral genome. This allows in principle cloning into the vector of up to 37 kb of foreign DNA. Recently the complete (19 kb) human α1 antitrypsin genomic DNA locus has been rescued in an Ad helper dependent vector (Ad HDV) (Schiedner et al., 1998) and its administration to mice resulted in long term expression of therapeutic levels of proteins.

The AAV DNA genome is a linear single-stranded DNA molecule having a molecular weight of about $1.5 \times 10^6$ daltons or approximately 4680 nucleotides long. The AAV2 genome has one copy of the 145 nucleotides long inverted terminal repeat (ITR) located at each end. The AAV ITR contain palindromic sequences that can fold over to form hairpin structures that function as primers during initiation of DNA replication. Additionally, the ITRs are needed for viral integration, rescue from the host genome, and encapsidation of viral nucleic acids into mature virions. Inserted in between the ITRs of AAV there is a unique region of about 4470 nucleotides that contains two main open reading frames (ORF). The right ORF encodes three capsid proteins VP1, VP2 and VP3. These three proteins form the viral particle and are produced from transcripts controlled by promoter $P_{40}$ located at map position 40. The left open reading frame of the AAV genome encodes the rep gene. Two promoters located at map positions 5 and 19 (promoters $P_5$ and $P_{19}$, respectively) control the expression of the four polypeptides derived from this ORF. Rep proteins Rep 78 and Rep 68 are produced from the $P_5$ promoted transcripts, and Rep proteins Rep 52 and Rep 40 are synthesized from the $P_{19}$ promoted transcripts. Srivastava et al. (1983) and Berns, K. I. (1996) provide the nucleotide sequence and organisation of the Adeno-Associated Virus 2 genome.

In the development of AAV vectors, it has been shown that the entire rep and cap domain can be excised and replaced with a reporter or a therapeutic transgene, and that the ITRs are the minimal signal sequence required for rescue, replication, packaging and integration of the AAV genome (Carter, B J.; Samulski J., R WO96/36364).

The development of AAV vectors for gene therapy has faced several limitations: difficulties encountered in the large scale production of replication defective recombinants, and the packaging limit of the AAV virion that cannot exceed 4.5 kb. This limitation excludes several larger genes which may be considered as potential candidates for gene therapy programmes.

Production of replication defective recombinants resulting from excision of cap and rep domain requires the cotransfection of two different complementing plasmids, one containing the gene for delivery (e.g. reporter or therapeutic gene) sandwiched between the two cis acting AAV ITRs, the second encoding the virus ORF for rep and cap peptides. Moreover, the cotransfected cell must also be infected with a helper virus (usually adenovirus or herpesvirus). While laboratory low production scale can be effectively achieved by cotransfection and infection, reproducible large scale production required for preparation of a therapeutic product is very difficult.

Additionally, recombinant AAV vectors in which rep and cap genes have been deleted do not integrate into the AAVS1 locus but they do so in a random fashion.

Targeting of integration involves the AAV rep gene products. In particular, the larger polypeptides Rep 78 and Rep 68 have been shown to bind in vitro the AAV ITRs and the aavsl, and possess helicase and site-specific endonuclease activities which may be required for AAV replication as well as AAV integration. See for example Shelling, A. N. et al (1994); Balagué, C., M. et al. (1997); Surosky, R. T. et al. (1997).

A possible alternative strategy is to transfer the ability for site-specific integration of AAV by transferring the appropriate viral genes and cis-acting signals required for site-specific integration into other large capacity viral vectors. Relevant elements of the AAV genome, such as the rep and cap ORF or the AAV ITRs, can be introduced into adenoviral vectors. The resulting recombinant Ad/AAV vectors would have the adeno larger packaging capacity, and the adeno characteristic ability to infect a large variety of cell types in vivo and of most eukaryotic cell lines in vitro.

A major stumbling block in the amplification of chimeric Ad/AAV vectors became apparent when it was realised that the AAV rep gene's expression has a toxic effect on Ad (De La Maza L. M. et al., 1978; Berns, K. I., 1996). Thus, the expression of the Rep gene during virus replication in 293 cells hinders the amplification of the Ad vector, by a mechanism that is not fully understood but is associated with the disruption of the Ad replication centres, identified by immunofluorescence and in situ hybridization studies (Weitzman M. D. et al., 1996.).

To avoid this difficulty, alternative strategies have been developed where the rep peptides are provided separately and are not encoded by the Ad/AAV vector. For instance, in WO96/13598 is disclosed a hybrid Ad/AAV virus which comprises portions of an adenovirus, 5' and 3' ITR sequences from an AAV and a selected transgene. Additionally, the hybrid virus is linked via a polycation conjugate to an AAV rep gene ("hybrid virus conjugate" or "transinfection particle"). The major drawback of these procedures is in the low efficiency and reproducibility of the conjugation process.

Other elaborate approaches have been attempted, emphasizing that the problem with producing Ad/AAV vectors is a severe one.

SUMMARY OF THE INVENTION

The present invention is founded on the surprising realisation that a much simpler approach can be taken to produce the desired vectors in large amounts, as successfully demonstrated experimentally.

The present invention provides in various aspects new procedures for the efficient preparation of recombinant helper dependent adenoviral vectors comprising AAV rep genes, based on the finding that it is possible to avoid rep inhibition of replication of viral vectors by keeping on separate replicating units the viral replication functions required for vector amplification and the AAV rep genes.

A general method according to one aspect of the present invention includes:

(a) providing cells containing a helper adenovirus vector;
(b) introducing a helper-dependent adenoviral vector including an AAV rep gene into the cells.

AAV rep 78 and/or rep 68 may be included in the helper-dependent adenoviral vector (Surosky, R. T. et al. 1997). rep50 and/or rep42 may additionaly be included. Modified forms of a rep gene which may encode a modified protein may be used, provided the ability of the protein to promote nucleic acid integration into the chromosome is retained. A modified form which is inactive or substantially inactive unless activated by means of an appropriate stimulus or signal may be employed.

Generally such a method is employed in production of adenoviral particles containing nucleic acid including the AAV rep gene, so that the method further includes incubating or cultivating the cells under conditions and for an appropriate length of time for production of such adenoviral particles. Adenoviral particles that are produced may be harvested, may be isolated and/or purified, and may be used as desired, e.g. in the formulation of a composition which may include one or more additional components, such as a composition (pharmaceutical) which includes one or more pharmaceutically acceptable excipients, vehicles or carriers (e.g. see below).

A substantially improved and preferred method further includes an additional step of pre-incubating the helper virus vector containing cells, for a period of time sufficient to allow expression of viral proteins required for Ad genome replication, before introducing the helper-dependent adenovirus vectors including an AAV rep gene.

Methods in accordance with the present invention are generally applicable to the preparation of vectors that by carrying one or more AAV rep genes have the property to inhibit adenovirus replication.

In a preferred method the helper is a helper adenovirus, and may be AdLC8cluc (Parks et al., 1996).

The optimal concentration of helper to be used in the method may vary, and if the helper virus genome is introduced into the host cell by DNA transfer methods, for each method a range of concentration may be used. If the helper genome is delivered by the use of infective viral particles, generally the range of concentration may be between 1 and 100 m.o.i. (multiplicity of infection), the preferred concentration being between 1 and 5 m.o.i.

The rep gene is or rep genes are generally under the control of a promoter, and most preferably under the control of a regulatable promoter. Suitable promoters include the α1-anti trypsin promoter, T7 promoter, and tissue-specific promoters. T7 promoter has a very low activity in the absence of the phage T7 polymerase and is an appropriate promoter to rescue adenovectors encoding toxic genes.

In preferred embodiments, the promoter is a tissue specific promoter that is known to be active in the cells of the target tissue (e.g. liver) but less active in the cell chosen as packaging cells for the production of the viral adenovectors.

The preparation of helper competent cells may achieved by infection of suitable cell lines with infective viral particles containing the helper virus genome. Alternatively, the helper virus genome may be delivered into the host cell using a variety of DNA transfer methods such as electroporation, DEAE-dextran, calcium phosphate, DNA gun, liposomes, etc.

The cell line that may be used as host is any cell line capable to sustain the replication of the helper and of the vector to be amplified. A preferred cell line is 293 for its ability to sustain defective adenovirus replication, in particular the 293 derived line 293cre (Chen L., et al., 1996). Use of this cell line selectively favors the packaging and amplification of helper dependent vectors which do not contain loxP sites at either end of the Adenovirus packaging signal. In contrast, packaging of a helper adenovirus such as AdLc8cluc is inhibited in this cell line, where the helper virus has been engineered to carry two loxP sites substrates of the Cre recombinase flanking the packaging signal (Parks et al. (1996) supra).

Instead of the cre-loxP recombinase system, other helper vectors may be employed based on the use of different recombinases and their specific substrate, and of suitable host cell lines. For example the yeast FLP recombinase and its recombinase sites may be used (O'Gorman et al. 1991).

In a preferred embodiment the invention relates to a selective timing of the delivery of the helper and of the helper-dependent vector to the same host cell to avoid replication inhibition due to AAV rep expression. An important part of this approach is the incubation time which extends from the time the helper virus is introduced into the cell line until the time the helper dependent adenoviral vector containing the rep gene is introduced into the cell line.

Generally this time should be sufficient for adenovirus early genes expression under the cultivation conditions. Standard conditions may be used, such as wherein infected 293cre cells are maintained in minimal essential medium (MEM) supplemented with 5% Horse serum (HS), 2 mM glutamine, 100 units/ml penicillin, and 100 mg/ml streptomycin. Cells are grown in tissue culture dishes (Falcon) at 37° C. in 5% $CO_2$.

Cells may be cultured for approximately between 0.5 and 12 hours, more preferably at least about 2 hours, maybe about 2–6 hours, or about 3–7 hours, and more preferably about 4 hours. Optimal timing may be established by monitoring the final titre in defective vector obtained, for example by setting up a series of growth experiment in parallel. For the preparation of viral particles containing a defective viral vector comprising an AAV rep gene, the viral vector genome is usually delivered to the helper infected cells by transfection in a first cycle, and by infection with infective viral particles containing the defective virus genome in successive cycles of amplification of the viral vector. (See e.g. Parks et al. 1996 supra.) Other DNA transfer method may be used, such as electroporation, DEAE-dextran, calcium phosphate, DNA gun, liposomes, etc.

Generally in the present invention, the viral vector is a recombinant Ad/AAV vector including one or more of the AAV rep genes, alone or in combination, under the control of a single or multiple regulatory elements. A preferred vector may be one selected from the group consisting of pRS1032; pRS1033; pRA1034 and pSTK (Schiedner et al., 1998) (see experimental section below).

The present invention also provides in further aspects host cells and cell lines infected with an Ad/AAV vector and Ad helper virus in accordance with the present invention.

The present invention also provides a system for replication and packaging in cultured cells of recombinant DNA into mature virions. Viral stocks containing recombinant DNA encapsidated into mature virions obtained by the methods here described represent further aspects of the present invention and can be used to transfer genetic information into any cell or tissue of choice.

Nucleic acid sequences can be readily prepared and manipulated by the skilled person using the information and references contained herein and techniques known in the art. In order to obtain expression of desired nucleic acid sequences for delivery, the sequences can be incorporated in a vector in accordance with the present invention having control sequences operably linked to the nucleic acid to control its expression. The vectors may include sequences such as promoters or enhancers to drive the expression of the inserted nucleic acid, and may include one or more further sequences so that the polypeptide is produced as a fusion and/or nucleic acid encoding secretion signals so that the polypeptide produced in the host cell is secreted from the cell. Suitable regulatory sequences, including promoter sequences, terminator fragments, polyadenylation sequences, enhancer sequences, marker genes and other sequences as appropriate, are available in the art. For further details see, for example, Sambrook et al., 1989. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., 1992. Marker genes such as antibiotic resistance or sensitivity genes may be used in identifying cells containing nucleic acid of interest, as is well known in the art.

Adenoviral particles containing nucleic acid encoding an AAV rep gene produced in accordance with the present invention may be formulated in pharmaceutical compositions. These compositions may comprise a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. intravenous, cutaneous or subcutaneous, nasal, intramuscular, intraperitoneal routes.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Following production of adenoviral particles containing nucleic acid encoding an AAV rep gene in according with the present invention, and optional formulation of such particles into compositions, the particles may be administered to an individual, particularly human or other primate.

This may be for a therapeutic purpose, e.g. in delivery of a functional gene encoding an authentic biologically active product in a method of gene therapy, to treat a patient who is unable to synthesize that product or unable to synthesize it at the normal level or in normal form, thereby providing the effect provided by the wild-type and ameliorating one or more symptoms of the relevant disease. Examples include provision of Factor VIII to a haemophiliac, or erythropoietin to an individual with chronic anaemia, chronic renal failure or sickle cell anaemia. Other therapeutically useful genes include those encoded Factor IX coagulation factor, LDL-receptor, insulin, dystrophin and CFTR.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition may be administered alone or in combination with other treatments, either simultaneously or sequentially dependent upon the condition to be treated.

Aspects and embodiments of the present invention will now be illustrated further with reference to exeperimental exemplification and the following figures. Further aspects and embodiments will be apparent to those of ordinary skill in the art.

The term "comprise" is used herein in the sense of "include".

DETAILED DESCRIPTION OF THE INVENTION

Figure 1:
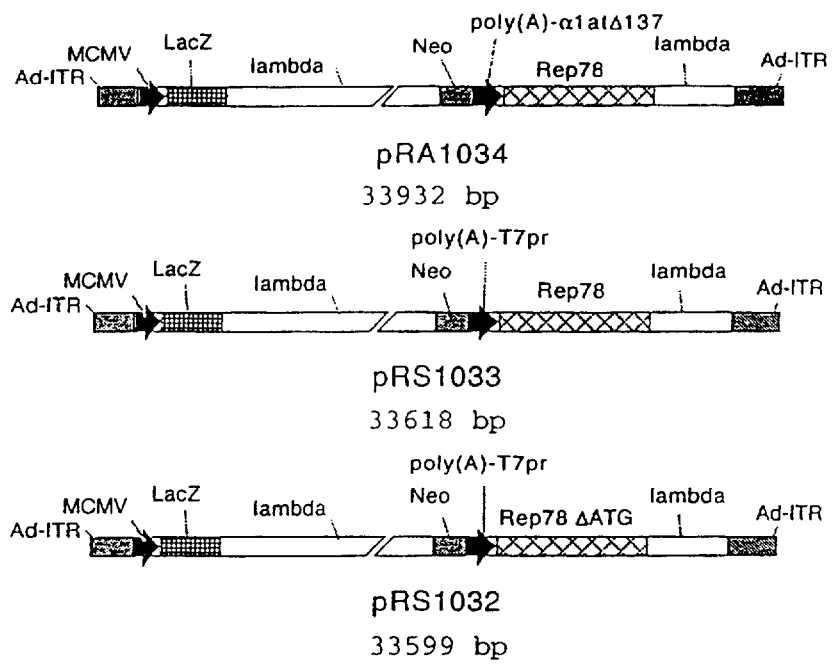
FIG. 1A shows a schematic representation of vector structures.
FIG. 1B shows the results of serial passage of Ad Rep vectors. pRP1030 was amplified as a positive control.
Figure 1:
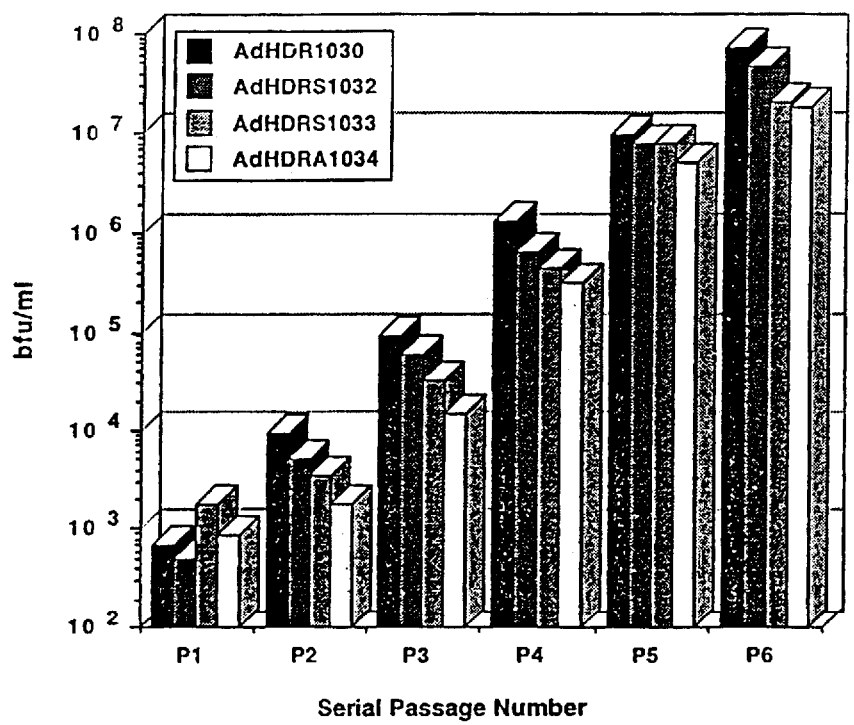

In the construction of viral vector useful for gene delivery such as in gene therapy, i.e. the transfer of genetic information into cells or tissues, one of the advantages offered by the AAV derived vectors is that the genetic material to be transfered can be directed to preferentially integrate in specific sites on the host chromosome. For this to occur the presence of at least one of the rep peptides is required, as discussed.

The present invention is based in part on observation that when cells containing genes coding for the rep AAV peptides are infected with Ad viruses, the expression of the rep genes results in the suppression of replication of the Ad viruses. This phenomenon is non-predictable, although in natural infection when Ad acts as helper for the rescue and replication of AAV a mechanism to down-regulate the replication of the helper is probably of advantage to the replicating AAV.

For the biotechnological development of recombinant AAV/Ad vectors the rep suppression poses a serious problem: amplification of any Ad vector is suppressed if rep peptides are present in sufficient amount in the cell. As noted above, different approaches have been taken to reduce or silence the rep gene activity.

With the development of helper dependent Ad vectors it has been possible to separate the viral replication functions required for vector amplification from the vector itself. The present invention is based on the discovery that if a rep gene from AAV is carried by a helper dependent Ad vector, its expression can be suppressed or delayed during the helper replication stage thus bypassing the inhibitory effect due to the rep gene expression.

The construction of the helper dependent Ad vectors carrying a rep gene here described for particular embodiments of the present invention, is based on the exploitation of the helper dependent Ad system described by F. Graham and coworkers (Parks et al. 1996). In brief, the helper dependent Ad system is based on the development of recombinant helper adenovirus that, when they are replicating in suitable cells, are able to produce all the proteins and RNA necessary to perform helper functions, but whose genome cannot be packaged in infective viral particles. This can be achieved by inserting artificial sites for specific recombinases (e.g. loxP sites target of Cre recombinase) on both sides of the helper packaging signals sequences. For example, the infection of a Cre expressing cell with an Ad virion containing the proper loxP sites, results in the derivation of cells expressing all the Ad helper function, but where the packaging of the helper genome is selectively imparted. Superinfection or transfection of such cells with an adeno helper dependent vector results in the replication and packaging of the helper dependent vector with minimal helper virus contamination.

EXAMPLE 1

Construction and Amplification of a First Generation Adenoviral Vector Carrying the Integration Cassette A plasmid denoted "pLBG40" contains the Ad5 genome deleted in E1 and E3 regions and is fully infectious when transfected in 293 cells. The E1–E3 deletions allow a theoretical insertion up to 6 kb of foreign DNA by direct cloning into unique restriction sites present in both E1 and E3 regions.

pLBG-ITRGFP/Hy Derivation (a) The AAV2-ITRGFP-HygroR cassette was constructed by inserting the humanized version of green fluorescent protein (GFP) gene driven by HCMV promoter from the pGreen Lantern plasmid (GIBCO BRL) and the Hygromicin B resistance gene fused to the Tk promoter between AAV2 ITRs in the context of plasmid pLITMUS28 (New England Biolabs) generating pITRGFP Hygro.

(b) The AAV2-ITRGFP/HygroR cassette was excised from pITRGFPHygro by XbaI-BglII digestion and cloned into XbaI-BamHI digested pABS.4 (Bett et al., 1994) generating pAB-ITRGFP/Hygro.

(c) The ITRGFP/Hygro cassette obtained from pAB-ITRGFP/Hygro by PacI digestion was inserted in the unique PacI restriction site of pLBG40, an Ad5 genome deleted of the E1 and E3 regions and fully infectious when transfected in 293 cells, generating pLB-ITRGFP/Hy.

Rescue of AdLB-ITRGFP/Hy (a) 60 mm dishes of semiconfluent monolayer of 293 cells were transfected with 3, 5, or 10 $\mu$g of pLB-ITRGFP/Hy using a standard calcium-phosphate technique (Graham F. L. et al. 1973).

(b) The cell monolayer was incubated overnight at 37° C., the medium was removed and 10 ml of medium-agarose overlay was added.

(c) Plaques were visible after 10 days of incubation at 37° C. Picking, screening and amplification of the isolated plaques were performed as described in Hitt, M. et al. 1995.

Analysis of Viral DNA

Purification of viral DNA from infected cells and purified virions was performed by digestion at 37° C. in proteinaseK/SDS buffer (10 mM Tris-HCl, pH7.5, 1 mM EDTA/1% SDS/1 mg/ml proteinaseK) followed by phenol extraction and ethanol precipitation. Episomal DNA was isolated from chromosomal DNA following the Hirt protocol (Hirt B., 1967).

EXAMPLE 2

Construction of Adenovirus Helper Dependent Vectors Carrying the AAV2Rep Gene

The Rep gene of AAV (Srivastava et al., 1983) was modified by point mutations to encode only the large polypeptide rep78 under the transcriptional control of the $\alpha$1-anti trypsin or T7 promoter (Horer, M., et al., 1995; De Simone, V., et al., 1987).

A hd Ad/Rep virus was constructed by insertion of the appropriately modified Rep gene into a hd Ad genome by restriction digestion.

Plasmids were constructed using standard protocols (J. Sambrook, et al. 1989).

pRP1030 Derivation

Plasmid pRP1030 was used as vector for the insertion of Rep expression cassette. It was derived from pRP1001 (Parks, et al. 1996) by deleting all Ad5 coding sequence and substituting it with a lambda phage DNA stuffer.

pRS1032 Derivation (a) The helper dependent plasmid pRS1032 was derived from pRP1030. It contains the insertion of a cassette constituted by Rep 78 ATG deletion mutant fused to T7 promoter. Rep 78 gene was obtained as described in Horer et al. (1995) by mutating the ATG start codon for Rep 52/40 to GGA (methionine>glycine, amino acid 225) and the G of the splice donor site for expression of spliced versions Rep 68/40 (nucleotide 1907) to A. Rep78$\Delta$ATG was obtained by PCR designed to delete the first ATG of the Rep open reading frame and fused to the T7 promoter in the context of the shuttle plasmid pABS-4 (Bett et al., 1994) generating pABT7-Rep78$\Delta$ATG.

(b) pABT7Rep78$\Delta$ATG: A PvuII fragment containing the T7Rep78$\Delta$ATG cassette was ligated into the unique StuI site of pRP1030 generating the Ad helper dependent plasmid pRS1032.

pRS1033 Derivation (a) The T7Rep cassette was constructed following the strategy reproted for T7Rep78$\Delta$ATG and inserted into the unique BamHI cloning site of pABS.4, generating pABT7Rep.

(b) pABT7Rep was converted in a Rep 78 expression vector by substituting the SfiI-XbaI DNA fragment with the SfiI-XbaI restriction fragment obtained from pCIIIRep78 plasmid. This fragment contains a mutation of the first ATG of Rep 52/40 (ATG-GGA) and a G>A mutation in the splice donor sequence present in the Rep ORF.

(c) The T7Rep78 cassette was than excised from pABT7Rep78 by PvuII digestion and inserted into the StuI site of pRP1030 generating pRS1033.

pRA1034 Derivation

The helper dependent plasmid pRA1034 was derived from pRP1030. pRA1034 contains rep 78 gene fused to a$\Delta$137$\alpha$1-antitrypsin promoter.

(a) $\alpha$1-antitrypsin ($\alpha$1-at)-Rep78 cassette was constructed by fusing rep78 gene to the $\Delta$137 $\alpha$1-at minimal promoter in the context of pABS-4 shuttle plasmid generating pRA1034.

(b) The $\alpha$1at-Rep78 cassette was then excised by PvuII digestion from pAB$\alpha$1at-Rep78 and cloned into pRP1030 generating pRA1034.

EXAMPLE 3

Rescue and Amplifications of Ad Helper-Dependent Vectors

Although the experiments directed to rescue of the T7Rep cassette into a first generation vector, E1 deleted adenoviral vectors were completely unsuccessful, an adenoviral vector carrying the AAV2 Rep78 gene were positively rescued and amplified following the Helper Dependent strategy.

Amplification of a hd Ad/Rep virus was obtained with a modification of the established protocol for the amplification of hd Ad viruses (Parks, R., et al., 1996). Semiconfluent monolayers of 293cre cells (Chen L, et al 1996) in 60 mm dishes were infected with AdLC8cLuc at a multiplicity of infection (m.o.i.) of 5 plaque-forming units (pfu)/cell.

4 hr after infection 293cre cells were transfected using standard calcium-phosphate technique with 5 $\mu$g of helper-dependent vector (pRS1032, pRS1033, pRA1034) for 6 hr at 37° C. The medium was replaced and the cells incubated until the monolayer showed complete cytopathic effect (CPE).

The cells were scraped into the medium and the virus released by freezing and thawing.

The resulting crude lysate was serially passaged on 60-mm dishes of 293cre cells as follows. During each round of amplification of the three different helper-dependent vectors, the 293cre monolayers were infected with AdLC8cLuc at an m.o.i. of 1 pfu/cell and incubated at 37° C. for 4 hr before the medium was removed and cells were incubated at 30° C. with an aliquot (500 $\mu$l) of the crude lysate obtained from previous passage.

Amplification was monitored at each passage by infecting 293 cells and counting lac-Z positive cells (blue forming unit (bfu), as described in Parks et al. (1996) (supra).

FIG. 1B shows the amplification results of the three Rep containing Helper-Dependent vectors in comparison with the non-recombinant vector RP1030.

The presence of Rep gene did not affect the amplification of the AdHD vector up to $1.8 \times 10^7$ b.f.u./ml (corresponding to 60–100 Rep78 expressing viral particles per cells). Time course of CPE was not affected by Rep virus infection and full CPE was usually achieved after 48–72 hours post-infection even during late passages in the presence of an increasing titre of Rep expressing viruses. The inhibition of Ad replication is mediated by Rep expression and dependent on the ratio of the multiplicity of infection of the two viruses and the temporal order of addition (Berns, K. I, 1996).

To reduce the Rep expression levels in the packaging cell line, and as direct consequence the detrimental effect on the vector production, the Rep gene was fused to $\Delta$-137 DNA fragment of $\alpha$1-antitrypsin promoter or to the T7 promoter. Although a residual Rep enzymatic activity was detected with both constructs by transfecting 293 cells, the protein was not detectable using a standard Western blot. Furthermore, to rescue the Ad viruses 293cre cells were first infected with the helper virus and than transfected with Rep plasmids 3–5 hr post-infection when the adenovirus early gene expression has already reached the peak (Sharp P. A, 1984). The same protocol was followed during the serial passages of the HD viruses.

To detect the presence of rearrangements involving the Rep expression cassette of the amplified HD vectors, the episomal DNA extracted from cell lysate at different passages was digested with DraI and analyzed by Southern blot using a Rep DNA probe. The detection of a single band of the expected size (6.3 Kb for AdHDRA1034, about 2.1 Kb for AdHDRS1032 and AdHDRS1033) demonstrated the integrity of the Rep cassette. No minor bands were detected after 48 hr exposure indicating that vector rearrangement did not occur during the serial passages.

Furthermore, the restriction pattern of the viral DNA analysed by agarose gel confirmed the structural integrity of the amplified vectors.

EXAMPLE 4

Functional Expression of Rep from Helper Dependent Adenovectors

Rep 78 expression was evaluated by Western blot, infecting Hep3B and as control HeLa cells with 50 b.f.u./cell of HdRA1034 or HdRS1032. Cells were harvested 36 hours post-infection and a Western blot analysis was performed on proteins extracted using a rabbit antiserum. pCIII-Rep78 containing the same gene fused HCMV promoter was transfected as positive control.

Rep 78 expression was detected in Hep3B but not in HeLa cells infected with HDRA1034 as expected. This result confirms the tissue specificity of the Rep78 gene fused to the liver specific $\alpha$1at promoter (De Simone et al., 1987).

EXAMPLE 5

Large Scale Vector Preparation

Large scale virus preparation was obtained by infecting 6 large 150 mm dishes with 500 ml of crude lysate approximately containing $10^7$ vector transducing particles. 4 hr before the incubation with the crude lysate the 293cre cells were infected with $10^7$ pfu of helper virus per 150 mm dish. After complete cytopathic effect the virus was purified as described (Hitt, M., et al. 1995) The total yield was $3 \times 10^9$ bfu from $5 \times 10^7$ cells, providing indication that 50–100 of Rep expressing virus per cell can be produced without interference problems.

EXAMPLE 6

Functional Analysis of the Helper Dependent Virus Expressing Rep78

The Rep78 protein is able to support in vitro the replication of AAV DNA in presence of an adenovirus-infected cell extract (Ni TH, et al. 1994). An assay of Rep 78 expression based on the rescue and replication of an AAV-ITRs flanked DNA in cells infected by adenovirus was used to demonstrate the functionality of HD Rep vectors amplified by serial passages in 293cre cells.

293 and 293cre monolayer were infected with about 0.5×10$^6$ b.f.u. using a crude lysate obtained from 293cre cells after 8 serial passages of vectors HDRP1030, HDRS1032, HDRS1033, HDRA1034. 4 hr later the cells were infected with the first generation vector AdLBGITR-GFP/Hy carrying the AAV ITR flanked transgene. As positive control, a dish of 293 cells infected with AdLBITR-GFP/Hy was transfected with pCIII-Rep 78, a plasmid containing an Human Cytomegalovirus (HCMV) promoter driven Rep 78 gene expression. At 48 hr post infection, episomal DNA was recovered and analyzed by Southern blotting using a DNA probe specific for the transgene.

The low molecular weight DNA bands observed in the southern blot corresponding to the size of AAV ITR/transgene cassette monomer and dimer demonstrated that 293 and 293cre cell lines were successfully infected by HDRS1033 and HDRS1034 and that Rep 78 protein was correctly expressed. The same signal was visible in the pCIII-Rep 78 transfection experiment, while in presence of the two control vectors HDRP1030 and HDRS1032 the rescue and replication did not occur—as expected.

EXAMPLE 7

Site Specific Integration Mediated by Helper Dependent Vectors Encoding Rep78

PCR Assay for AAVS1 Integration

A nested PCR based assay on genomic DNA was set up to detect junctions between the AAVS1 and AAV ITRs. Two pairs of primers specific for AAVS1 and AAV ITRs have been used. HepG2 or Huh7 cells were infected first at an moi of 1 bfu/cell with HdRS1032 or HdRA1034 and 3–4 hours later with moi 1 pfu/cell of AdLB-ITRGFP/Hy. Cells were harvested by scraping 48 hours after infection and total DNA extracted by standard techniques (Sambrook J. et al. T. 1989) Nested PCR was performed on 1 µg of cellular DNA in a reaction mixture containing 1.25 U of AmpliTaq Gold (Perkin Helmer), 1×ampliTaq Gold buffer, 2.5 mM MgCl$_2$, 200 mM of deoxynucleoside triphosphates and 50 pmol of each primer. Amplification conditions were: 10 min at 94° C. followed by 25 cycles of 94° C. for 1 min, 60° C. for 1 min and 72° C. for 2 min. The second step of amplification was done using 10 µl of the first reaction following the reported reaction conditions.

AAVS1 primers were:

15a (5'-GCTCTCAGAAGCCAGTAGAGC-3'; SEQ. ID. No. 1) and Cr2shift (5'-CTGGCTCAGGTTCAGGAGAGG-3'; SEQ. ID. No. 2).

Primers 16s (5'-GTAGCATGGCGGGTTAATCA-3'; SEQ. ID. No. 3) and 17s long (5'-TTAACTACAAGGAACCCCTAGTGATGG-3'; SEQ. ID. No. 4)

were derived from AAVITR sequence.

1/10 of the amplified DNA was loaded in duplicate on 1.3% agarose gel, transferred HybondN+ membrane (Amersham) and hybridized with an AAVS1 or AAV ITR probes.

AAVS1 DNA probe was labelled by random priming with $^{32}$P (Multiprime, Amersham). AAVITR probe was obtained with two primers derived from pSUB201 (nts 1-119) labelled with $^{32}$P by fill-in reaction in presence of 5 U of Klenow fragment of DNA polymerase and 50 µCi of 32PdATP and 32PdCTP (NEN).

Site-specific Integration of AAV-ITR Transgene

Cell transfections with plasmids demonstrated that Rep expressed from a cassette located outside viral ITRs can act in trans promoting site-specific integration of an AAV-ITRs-flanked transgene. The results demonstrate that Rep 78 expressed from HDRA1034 mediates integration of the rescued transgene in AAVS1 locus.

HepG2 and HuH7 cells were coinfected with HdRA1034 and Ad LBITR-GFP/Hy. 48 hours post-infection cells were harvested and genomic DNA extracted. A nested PCR-based assay on genomic DNA was set up to detect junctions between AAVS1 and viral ITRs. Two pairs of primers specific for AAVS1 and AAVITRs were used. AAVS1 primer sequences was chosen in the DNA sequence located downstream the 100-bp AAVS1 region identified as "hot spot" for site specific integration (Samulski R. J. et al. 1991). Amplified DNA was loaded on agarose gel in duplicate and analyzed by Southern blot using either AAVS1 or AAVITR specific probes.

Similar results were observed upon infection of Huh7 and HepG2 cells. Positive signals were detected only in cells infected with Rep expressing virus. No AAVS1-AAVITR junctions were amplified from cells infected with HDRA1032 carrying the Rep78ΔATG mutant or with AdLBGITR-GFP/Hy alone. The hybridization patterns appeared to be identical with both probes suggesting that different AAVS1-AAVITR junctions were actually amplified. Three major bands ranging in size between 500 bp and 100 bp superimposed on a smear were detected, with the major species being approximately 100 bp.

Amplified DNA was eluted from the gel, cloned and sequenced. The sequence data confirm that the amplified DNA contain the junction between the AAVS1 genomic region and the AAV ITR.

Fluorescence in Situ Hybridization (FISH) of Infected Cells

A 3.7 kb DNA fragment corresponding to the transgene cassette and a 80 kb AAVS1 DNA fragment isolated by screening a genomic DNA library were labelled using Nick Translation Kit (Boehringer Mannheim) according to the manufacture's instruction and used as probes in chromosome analysis. The chromosome spreads from a pool of hygromicin resistant HepG2 cells were prepared by standard cytogenetic techniques (Lawrence et al., 1988).

Cytogenetic preparations were pre-treated with RNase A solution (10 mg/ml in 2×SSC), with Pepsin solution (0.005% in 10 mM HCl) and dehydrated through 70, 90 and 100% ethanol. The preparations were then denatured using a 70% deionized formamide solution and dehydrated again through cold ethanol at increasing concentration.

For each sample, 300 ng of probe specific for the transgene cassette and 100 ng of probe specific for the AAVS1 sequence, respectively biotin and digoxigenin labelled, were precipitated with 10× excess of Cot1 human DNA (Gibco) and 10× excess of sonicated salmon sperm DNA and then resuspended in hybridization solution (50% formamide, 2×SSC and 10% Dextran Sulphate). Probes were denatured 5 minutes at 75° C. and subsequently incubated for 10 minutes at 37° C. to allow preannealing of repeated sequences. Finally the hybridization solution was placed on the samples, covered with coverslips and incubated overnight at 37° C. in a moist chamber.

The samples were then washed three times in 50% formamide/2×SSC and three times in 2×SSC in a water bath at 37° C. Visualization of biotin-labelled probe was carried out by an incubation with Cy3-Avidin (Amersham). The digoxigenin-labelled probe was detected using a sheep anti-digoxigenin antibody FITC-labelled (Boehringer Mannheim).

After immunodetection, slides were counterstained with 100 ng/ml of 4',6'-diamidino-2-phenylindole (DAPI). Ultraviolet excitation was used to locate metaphases and photographic images were taken by a CCD camera (Princeton Instruments, Inc.) using green (FITC signal) or blue violet (Cy3 signal) illumination.

Images were processed using Adobe Photoshop on a Apple Power Macintosh computer.

Assessment of Site-specific Integration by FISH Analysis

Since FISH analysis permit the direct study of chromosomal localization of a single copy gene, this technique was used to confirm AAV-ITR transgene integration in chromosome 19. For this purpose, AdLBGITR-GFP/Hy was substituted with an helper dependent vector, HdFB1, derived from the pSTK120 helper dependent plasmid carrying the same transgene. A system based on two helper dependent vector allowed the elimination of the toxic effect of leaky expression and replication of ΔE1 Ad in HepG2 cells (Sprengel R. et al. 1991). Since Rep expression exerts a cytostatic activity, to develop stable clones with a system based on double infection a strategy was chosen aimed to maximize the probability of cell co-infection avoiding high Rep gene copy number.

HepG2 cells were co-infected with 5 transducing unit/cell of HDRA1034 or HDRS1032, the lowest moi compatible with 80/90% cell infection, in combination with the same moi of HdFB1.

FISH analysis was performed after several passaging of cells in presence of hygromicin B.

AAVITR transgene was detected in 6 out of 16 different metaphase spreads on one allele of chromosome 19.

In summary, the present inventors have succeeded in providing an approach for generation of novel hybrid Ad/AAV vectors encoding the AAV Rep78 gene, which are able to mediate site specific integration of a ITR-flanked DNA.

REFERENCES

Ausubel et al. (1992). Current Protocols in Molecular Biology, John Wiley & Sons
Balagué, C., et al. (1997). *J. Virol.* 71, 3299–3306.
Berns, K. I. (1996) in *Virology*, ed. Fields, B. N., Knipe, D. M., Howley, P. M., Chanock, R. M., Melnick, J. L., Monath T. P., Roizman B., Straus, S. E. (Lippincott-Raven, Philadelpia) 3rd ed., pp. 2173–2197.
Bett A. J., et al. (1994) *Proc.Natl.Acad.Sci. USA* 91, 8802–8806.
Carter, B J. in "Handbook of Parvoviruses", ed. P. Tijsser, CRC Press, pp. 155–168.
Chen L, et al (1996) Somat. Cell. Mol. Genet., 22, 477–488.
Graham F. L. et al. (1973) *Virology* 52, 456–467
De La Maza L. M. et al. (1978) In: Ward D., Tattershall P., ed. Replication of mammalian parvoviruses. Cold Spring Harbor, N.Y: Cold Spring Harbor Laboratoty Press, 1978; 193.
De Simone V., et al (1987) *EMBO J.* 6, 2759–2766.
Hirt B. (1967) J.Mol. Biol. 26:365–369.
Hitt, M., et al. (1995) in *Methods in Molecular Genetics*, ed. Adolph, K. W. (Academic, San Diego), Vol.7, 13–30.
Horer M., et al.(1995) *J.Virol.* 69,5485:5496. Lawrence J. B., et al. (1988). *Cell* 52: 51–61.
Kotin, R. M., et al. (1990) *Proc. Natl. Acad. Sci. USA* 87, 2211–2215.
Ni T. H., et al. (1994) *J Virol.* 68, 1128–1138.
O'Gorman et al. (1991) *Science* 251: 1351.
Parks R. J., et al (1996) *Proc.Natl.Acad.Sci. USA* 93, 13565–13570.
Remington's Pharmaceutical Sciences, 16th edition, Osol, A. (ed), 1980
Sambrook J. et al. (1989) *Molecular Cloning: A Laboratory Manual.* (Cold Spring Harbor Lab. Press. Plainview, N.Y.) 2nd Ed.
Samulski R. J. et al. (1987) *J. Virol.* 61,3096–3101.
Samulski, R. J., et al (1991). *EMBO J.* 10, 3941–3950.
Samulski R. J., R WO96/36364).
Schiedner G., et al. (1998) *Nature Gen.* 18,180–183. Sharp P. A. (1984). "The Adenoviruses", (H. S. Ginsberg, ed.) 172–204, Plenum Press, New York, London.
Shelling, A. N., et al. (1994). *Gene Ther.* 1, 165–169.
Sprengel J. M. et al. (1991) *Proc.Natl.Acad.Sci.USA* 88,6472–647.
Srivastava et al. (1983) *J. Virol:* 45,555.
Surosky R. T., et al (1997) *J.Virol.* 71,7951–7959.
Weitzman M. D., et al. (1996) *J. Virol.* 70,1845–1854.

What is claimed is:

1. A method of producing adenoviral particles, the method comprising:
   (a) providing cells in vitro comprising a helper adenovirus vector for a helper-dependent adenovirus vector;
   (b) pre-incubating the cells comprising helper adenovirus vector to allow expression of viral proteins required for adenoviral genome replication before step (c);
   (c) introducing a helper-dependent adenoviral vector comprising an Adeno-Associated Virus (AAV) rep gene into the cells; and
   (d) incubating the cells to produce adenoviral particles containing nucleic acid comprising the AAV rep gene.

2. A method according to claim 1 wherein the pre-incubation is for a time of between 0.5 and 12 hours.

3. A method according to claim 2 wherein the pre-incubation is for a time of about 2–6 hours.

4. A method according to claim 1 wherein the pre-incubation is for a time of at least about 2 hours.

5. A method according to claim 4 wherein the pre-incubation is for a time of about 4 hours.

6. A method according to claim 1 wherein the helper-dependent adenoviral vector comprises a rep 78 gene.

7. A method according to claim 1 wherein the helper-dependent adenoviral vector comprising an AAV rep gene is introduced into the cells by infection with infective viral particles.

8. A method according to claim 1 further comprising the step of harvesting adenoviral particles from the cells of step (d).

9. A method according to claim 8 wherein harvested adenoviral particles are formulated into a composition comprising said harvested adenoviral particles.

10. A method according to claim 9 wherein the composition comprises a pharmaceutically acceptable excipient, vehicle or carrier.

11. A method according to claim 1 wherein the adenoviral particles comprise nucleic acid encoding a therapeutic protein.

12. A method according to claim 1 where said Rep gene is under the control of a tissue specific promoter that is less active in said cells than in cells of the tissue.

13. A method according to claim 12 wherein said promoter is alpha 1-anti-trypsin promoter.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
gcgcgcagaa gccagtagag c                                            21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
```

```
ctggctcagg ttcaggagag g                                         21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
gtagcatggc gggttaatca                                           20

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 4
ttaactacaa ggaaccccta gtgatgg                                   27
```